United States Patent [19]

Teicher

[11] Patent Number: 4,985,416
[45] Date of Patent: Jan. 15, 1991

[54] PLATINUM COMPLEXES OF AZODIAZONIUM DYES AS ANTI-TUMOR AGENTS

[75] Inventor: Beverly A. Teicher, Needham, Mass.
[73] Assignee: Dana Farber Cancer Institute, Inc., Boston, Mass.
[21] Appl. No.: 322,768
[22] Filed: Mar. 13, 1989
[51] Int. Cl.$^5$ .................. C07C 245/20; A61K 31/655
[52] U.S. Cl. ...................................... 514/150; 534/562
[58] Field of Search .................... 534/562; 514/150

[56] References Cited

U.S. PATENT DOCUMENTS 1,889,298  11/1932  Schnitzpahn I .............. 534/562

FOREIGN PATENT DOCUMENTS

| 569205 | 1/1933 | Fed. Rep. of Germany | 534/562 |
| 865451 | 7/1949 | Fed. Rep. of Germany | 534/562 |
| 132204 | 6/1929 | Switzerland | 534/562 |
| 132205 | 6/1929 | Switzerland | 534/562 |
| 132209 | 6/1929 | Switzerland | 534/562 |
| 132212 | 6/1929 | Switzerland | 534/562 |

OTHER PUBLICATIONS

Richmond et al., Radiation Research, vol. 71, 447–460, (1977).
Bernal et al., Science, vol. 222, 169–172, (1983).
Teicher et al. I, Int. J. Rad. Onc. Biol. Phys., vol. 11, 937–941, (1985).
Teicher et al. II, Int. J. Rad. Onc. Biol. Phys., vol. 13, 1217–1224, (1987).
Teicher et al. III, Rad. Res., vol. 109, 58–67, (1987).
Teicher et al. IV, Biochem. Pharmacol., vol. 35, 3365–3369, (1986).

Primary Examiner—Floyd D. Higel
Attorney, Agent, or Firm—Fish & Richardson

[57] ABSTRACT

Complexes having the structure

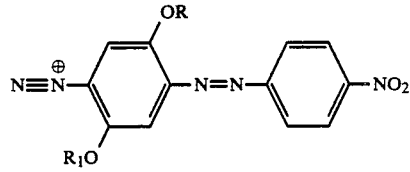

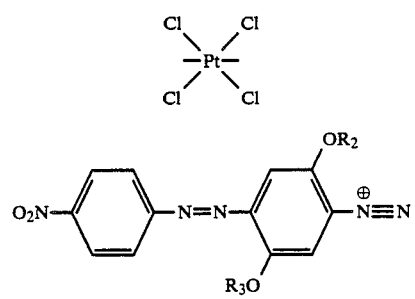

in which R, $R_1$, $R_2$, $R_3$ represent lower alkyl groups are cytotoxic to tumor cells in mammals and enhance the killing effect of radiation and heat.

6 Claims, No Drawings

PLATINUM COMPLEXES OF AZODIAZONIUM DYES AS ANTI-TUMOR AGENTS

This invention was made with Government support and the Federal Government has certain rights in the invention.

This invention relates to complexes of bivalent platinum and nuclear dyes useful in delaying growth of tumors in mammals and in enhancing the killing of tumor cells by radiation therapy and/or hyperthermia.

Cis-diamminedichloroplatinum (II) and certain organic complexes of the tetrachloroplatinate dianion have long been known as anti tumor drugs as well as enhancers of the effect of radiotherapy on tumors, Richmond et al., Radiation Research, Vol 71, 447–460 (1977); and mitochondrial dyes such as Rhodamine 123 have also been reported to be selectively by retained by and selectively toxic toward carcinoma cells by Bernal et al., Science, Vol 222, 169–172 (1983). Complexes of tetrachloroplatinate with Rhodamine 123 and certain other mitochondrial dyes have been reported to have good anti-tumor activity in the absence of radiation; of these, the Rhodamine-123 complex has been indicated to be the most effective in enhancing cell killing by radiation because of its relatively low level of whole-mammal toxicity and its relatively high level of radiation enhancement. Teicher et al., Int. J. Rad. Onc. Biol. Phys., Vol 11, 937–941 (1985); Teicher et al., Ibid., Vol 13, 1217–1224 (1987); Teicher et al. Rad. Res., Vol. 109, 58–67 (1987); Teicher et al., Biochem. Pharmacol., Vol 35, 3365–3369 (1986).

However, the generally accepted rule is that clinical hypoxic cell radiation sensitizers should be non toxic at effective sensitizing concentrations; this has militated against clinical use of previously known dye complexes with platinum.

It has now been found that ionically neutral complexes of tetrachloroplatinate bivalent anion with cationic nitro aromatic azoic diazo nuclear dyes are both effective anti-tumor agents in the absence of radiation and also effective sensitizers to or enhancers of subsequent radiation or heating, and have a high therapeutic index, as indicated by the wide range of dosage which is effective but non-lethal and the lack of toxicity to bone marrow. The preferred complexes of the present invention have the composition shown below.

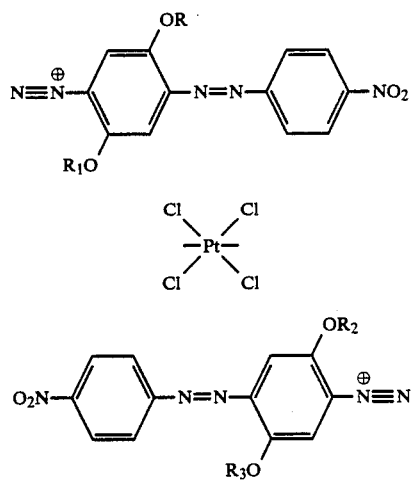

in which R, $R_1$, $R_2$, and $R_3$ are lower alkyl groups having 1–5 carbon atoms. Most preferred is the complex made with the nuclear dye Fast Black, hereinafter referred to as Pt(Fast Black)$_2$ which has the composition shown above in which R, $R_1$, $R_2$, and $R_3$ are all methyl groups.

The complexes of the present invention can be made simply by adding a slight molar excess of the dye to potassium tetrachloroplatinate in water at room temperature and allowing the mixture to stand. The desired complex precipitates.

The complex of the present invention can be administered by percutaneous injection; when employed in conjunction with radiation or heat it is preferably administered within a few hours before exposure to radiation or heat although there is nothing critical about the time interval between the two. It can be administered in solution in any pharmacologically acceptable carrier.

The effective dose may vary over a wide range, varying from 50 mg/kg of body weight up to the maximum tolerated dose (i.e. the $LD_{50}$) which is of the order of 600 mg/kg. The optimum dose in any case can be determined by routine tests and is far higher than the maximum tolerated dose for the dye alone.

The following specific example is intended to illustrate the nature of the invention without acting as a limitation upon its scope.

EXAMPLE

Fast Black Potassium Salt (Aldrich) (0.92 g, 0.0022 mol.) was dissolved in water (15 ml.). To this solution was added a solution of potassium tetrachloroplatinate (0.42 g, 0.001 mol.) in 10 ml. of water. A precipitate formed immediately, and after stirring for 30 minutes the precipitate was collected by suction filtration, washed with ice cold water (20 ml.), methanol (20 ml.). and diethyl ether (20 ml.). Yield of the complex Pt (Fast Black)$_2$ was 1.10 q (57% based on platinum). Analysis: Calc : C 34.85%, H 2.48%, N 14.50%, Pt 20.20%. Found: C35.07%, H 2.48%, N 14.08%, Pt 19.91%. I.R. and U.V. absorption spectra and H-nmr data were consistent with the structure shown above.

Anti-tumor activity of the complex prepared as described above was determined in vivo in mice by comparative tests against Fast Black dye alone and against Cis-diamminedichloroplatinum (CDDP) using the following procedure Two different solid tumor cell lines were employed, Lewis Lung and FSaII, $2 \times 10^6$ tumor cells being implanted i.m. into the legs of male C57BL/6J and C3H/He mice 8 to 10 weeks of age, respectively. The drugs were administered i.p. on day 7 after tumor implantation (when tumors were about 100 mm$^3$ in volume), in solution (0.5%) in 0.9% phosphate-buffered saline as carrier. Tumor growth delay is reported in Table I below as the difference in number of days for the treated tumors to reach 500 mm$^3$ in volume and the number of days required for untreated control tumors to reach the same volume (n=14 in each group). Tumor volume was calculated as a hemiellipsoid. In the control animals, tumors reached the specified volume in 12–14 days.

TABLE 1

| Drug | Dose mg/kg | Mean No. Days Delay | |
|---|---|---|---|
| | | Lewis Lung | FSaII |
| Pt (Fast Black) | 500 | 8.7 | 5.6 |
| | 250 | 7.6 | 5.1 |
| | 100 | 6.6 | 4.6 |

TABLE 1-continued

| Drug | Dose mg/kg | Mean No. Days Delay Lewis Lung | FSaII |
|---|---|---|---|
| Fast Black Dye | 250 | 2.0 | 2.7 |
|  | 100 | — | — |
|  | 50 | — | — |
| CDDP* | 10 | <1 | 8.0 |
|  | 5 | <1 | 4.4 |

*CDDP = Cis-diamminedichloroplatinum (II)

Anti-metastatic activity was determined by implanting Lewis Lung carcinoma cells in the legs of mice as described above, administering drugs in the doses indicated in Table II below, i.p. on day 7 after implantation and removing the lungs on day 20 followed by counting metastases. Control mice received no drug (n=14 in each group). The results were as follows:

TABLE 2

| Drug | Dose mg/kg | Mean No. of Metastases per Animal |
|---|---|---|
| None (control) | — | 14 |
| Pt (Fast Black)2 | 500 | 0.6 |
|  | 250 | 2.4 |
|  | 100 | 4.8 |
| Fast Black | 250 | 11.0 |
|  | 100 | 12.3 |
|  | 50 | 13.3 |
| CDDP | 10 | 10.7 |
| CDDP | 5 | — |

Effectiveness of the Pt (Fast Black)2 complex as a radiosensitizer or radiation enhancer in vivo was determined in comparison with Fast Black alone and with misonidazole, a nitroimidazole enhancer, by measuring growth delay in mice. FSaII fibrosarcoma cells (2×10⁶ FSaII cells) were implanted in the legs of mice: the drug was administered i.p. when the tumor had grown to approximately 50 mm³ in volume, using 0.9% phosphate buffered saline as carrier, as described above in the doses shown in Table 3 below. Fifteen minutes later radiation was delivered locally to the tumor bearing limb as a single dose of 10, 20, or 30 gray as indicated in the table. No anesthetic was used. The growth of each tumor was measured thrice weekly until it reached a volume of 500 mm³. Each treatment group had 7 animals and the procedure was repeated 3 times. Tumor volume was calculated as a hemiellipsoid, and in the untreated control animals, tumors reached the specified volume in 14.0 days. The delay is reported in terms of the mean number of additional days beyond the control required for the tumors in each group to reach the specified volume. The results were as follows:

TABLE 3

| Drug | Dose mg/kg | Single Radiation Dose, Gray | Mean No. Days Delay |
|---|---|---|---|
| — | — | 0 | 0 |
| Pt (Fast Black)2 | 500 | 0 | 5.6 |
| Fast Black | 300 | 0 | 3.0 |
| MSA* | 1000 | 0 | 1.6 |
| — | — | 10 | 1.8 |
| Pt (Fast Black)2 | 500 | 10 | 16.5 |
| Fast Black | 300 | 10 | 7.0 |
| MSA* | 1000 | 10 | 3.8 |
| — | — | 20 | 6.3 |
| Pt (Fast Black)2 | 500 | 20 | 21.0 |
| Fast Black | 300 | 20 | 12.6 |
| MSA* | 1000 | 20 | 7.6 |
| — | — | 30 | 8.8 |
| Pt (Fast Black)2 | 500 | 30 | 26.6 |
| Fast Black | 300 | 30 | 16.2 |

TABLE 3-continued

| Drug | Dose mg/kg | Single Radiation Dose, Gray | Mean No. Days Delay |
|---|---|---|---|
| MSA* | 1000 | 30 | 13.9 |

*MSA = Misonidazole

The complex was also found to be effective in enhancing the killing effect of heat treatment (hyperthermia) in vivo. The procedure described in the preceding paragraph was carried out except that there was substituted for the single radiation dose a heat treatment by immersion of the tumor-bearing limb in a water bath at 44° C. for 30 minutes to raise the tumor temperature to 43° C. The means number of days delay (n=14) was as follows:

TABLE 4

| Drug | Dose mg/kg | Heat 30 Min. at 43° C. | Mean No. Days Delay |
|---|---|---|---|
| — | — | Yes | 1.4 |
| Pt (Fast Black)2 | 500 | No | 5.6 |
| Pt (Fast Black)2 | 500 | Yes | 11.0 |
| Pt (Fast Black)2 | 100 | No | 4.6 |
| Pt (Fast Black)2 | 100 | Yes | 9.4 |
| Fast Black | 300 | No | 2.7 |
| Fast Black | 300 | Yes | 4.4 |
| CDDP | 5 | No | 4.4 |
| CDDP | 5 | Yes | 5.9 |

Analysis of EMT6 cells exposed to the complex of the example showed that entry of platinum into the cells was approximately 100 times as great as in the case of exposure to Cis-diamminedichloroplatinum (II) at the same concentration and exposure time; exposure to potassium tetracloroplatinate provised only very poor entry of platinum into the cells.

Cytotoxicity assays on the well-established EMT6 mammary tumor cell line under normally oxygenated conditions and hypoxic conditions at both pH 7.40 and pH 6.45 showed Pt (Fast Black)2 to be moderately cytotoxic, killing 1 log of hypoxic cells at 500 $\mu$m for 1 hour and 1.5 logs of normally oxygenated cells at pH 7.4; at pH 6.45 however, the pH level expected in hypoxic areas in tumors, there were approximately 3.5 logs of cell kill in both normally oxic and hypoxic cells. The Pt (Fast Black)2 complex of the example efficiently produces single strand breaks in DNA and associates with the DNA in such a way that the electrophoretic mobility of the DNA is altered and ethidium bromide binding is inhibited.

What is claimed is:

1. The method of increasing the susceptibility of tumor cells in a mammal to killing by exposure to radiation or heat which comprises injecting into said mammal a composition comprising (1) a complex having the composition

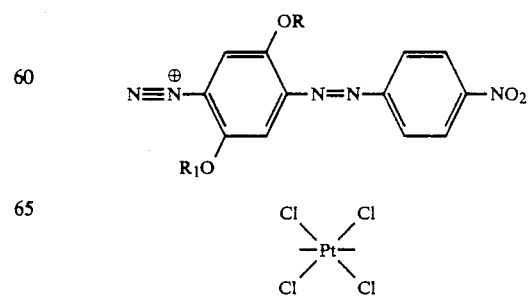

-continued

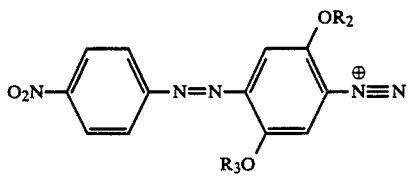

in which R, $R_1$, $R_2$, and $R_3$ are lower alkyl groups having 1-5 carbon atoms, together with 92) a pharmacologically acceptable non-toxic carrier therefor.

2. The method as claimed in claim 1 in which R, $R_1$, $R_2$, and $R_3$ are methyl groups.

3. The method of increasing the susceptibility of tumor cells in a mammal to killing by radiation which comprises injecting into said mammal a composition comprising (1) a complex having the composition

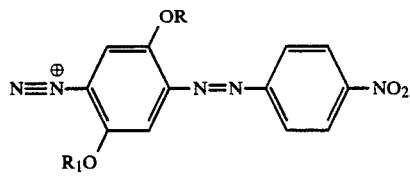

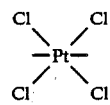

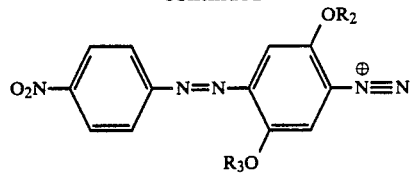

in which R, $R_1$, $R_2$, and $R_3$ are lower alkyl groups having 1-5 carbon atoms, together with (2) a pharmacologically acceptable non-toxic carrier therefor.

4. The method as claimed in claim 3 in which R, $R_1$, $R_2$, and $R_3$ are methyl groups.

5. The method of increasing the susceptibility of tumor cells in a mammal to killing by heat which comprises injecting into said mammal composition comprising (1) a complex having the composition

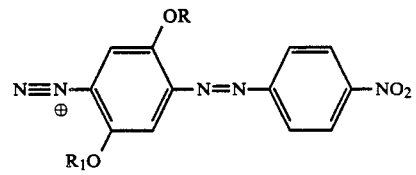

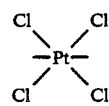

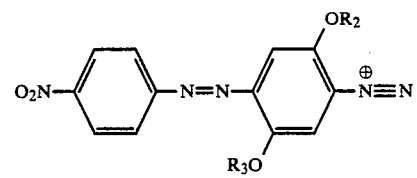

in which R, $R_1$, $R_2$, and $R_3$ are lower alkyl groups having 1-5 carbon atoms, together with (2) a pharmacologically acceptable non-toxic carrier therefor.

6. The method as claimed in claim 5 in which R, $R_1$, $R_2$, and $R_3$ are methyl groups.

* * * * *

UNITED STATES PATENT AND TRADEMARK OFFICE
CERTIFICATE OF CORRECTION

PATENT NO. : 4,985,416

DATED : January 15, 1991

INVENTOR(S) : Beverly A. Teicher

It is certified that error appears in the above-identified patent and that said Letters Patent is hereby corrected as shown below:

Col. 5, line 15; "92)" should be --(2)--

Signed and Sealed this

First Day of September, 1992

Attest:

DOUGLAS B. COMER

*Attesting Officer*  *Acting Commissioner of Patents and Trademarks*